United States Patent [19]

Clemens

[11] 4,069,814
[45] Jan. 24, 1978

[54] DOUBLE LUMEN CANNULA APPARATUS

[75] Inventor: Anton Hubert Clemens, Elkhart, Ind.

[73] Assignee: Miles Laboratories, Inc., Elkhart, Ind.

[21] Appl. No.: 683,642

[22] Filed: May 6, 1976

[51] Int. Cl.² .............................................. A61B 5/14
[52] U.S. Cl. .............................. 128/2 F; 128/DIG. 5;
128/214 R; 128/240
[58] Field of Search ................. 128/2 F, DIG. 5, 276,
128/221, 214 R, 214.4, 214.2, 240

[56] References Cited

U.S. PATENT DOCUMENTS

| 2,614,563 | 10/1952 | Devine, Jr. | 128/276 |
| 3,081,770 | 3/1963 | Hunter | 128/2 F X |
| 3,512,517 | 5/1970 | Kadish et al. | 128/DIG. 5 |
| 3,610,226 | 10/1971 | Albisser | 128/2F |
| 3,955,573 | 5/1976 | Hansen et al. | 128/276 |
| 3,958,566 | 5/1976 | Furihata | 128/2 F X |

Primary Examiner—Kyle L. Howell
Attorney, Agent, or Firm—Louis E. Davidson

[57] ABSTRACT

Double lumen cannula apparatus for blood sampling is described having the improvements of apparatus features for obtaining controlled dilution of the blood sample with an anti-coagulant and a minimal volume for a chamber introducing the anti-coagulant to the cannula.

7 Claims, 1 Drawing Figure

DOUBLE LUMEN CANNULA APPARATUS

BACKGROUND AND PRIOR ART

In hospital and clinical establishments, as well as in research situations, it is frequently necessary to slowly withdraw blood samples from a human patient or an experimental animal over an extended period of time. This is conveniently accomplished by inserting a cannula into a blood vessel, such as a vein or an artery, of the patient or animal and withdrawing the blood as desired from the cannula. In order to prevent blood coagulation in the cannula or in associated tubing for conducting the blood sample from the cannula, it is usual practice to mix an anticoagulant material, such as heparin, with the blood sample as soon as possible after it is withdrawn from the blood vessel. For this purpose a double lumen cannula apparatus has been used for many years. In this double lumen apparatus a smaller diameter tube is inserted within the usual cannula sheath. The passage through this smaller diameter tube forms one lumen, and the annular space between the outer wall surface of the inner tube and the inner wall surface of the cannula sheath forms the other lumen. The inner tube terminates within the cannula sheath a short distance from the tip of the cannula sheath. In use, the anti-coagulant material passes through the annular lumen toward the tip of the cannula sheath where it contacts and mixes with the blood entering the cannula from the blood vessel. The mixture of blood and anti-coagulant material then flows out of the cannula through the inner tubular lumen of the double lumen cannula apparatus.

The prior art double lumen cannula apparatus, had two principal disadvantages. First, the distance between the end of the inner tubular lumen and the tip of the cannula sheath was not controlled with any high degree of precision. Most double lumen cannula apparatus have a support body through which the inner tubular lumen and a conduit for anti-coagulant material are passed. The cannula sheath which normally has a funnel portion at one end and a tubular portion at the other end is mated in a conical press-fit against the body so that the inner tubular lumen is located coaxially within the tubular portion of the cannula sheath. Any variations in the length of the cannula sheath and/or of the inner tubular lumen or of the conical press-fit between the cannula sheath and body can cause a variation in the distance between the end of the inner lumen and the tip of the cannula sheath. If this distance is undesirably low, some of the anit-coagulant material from the annular lumen might undesirably enter the blood vessel of the patient or animal. There would also be inadequate dilution of the blood sample by the anti-coagulant material. This can cause false readings when the diluted blood sample is subsequently analyzed. If the distance is undesirably large, some of the blood start to coagulate in the cannula sheath before it contacts the anti-coagulant material.

This undesirable variation in distance is achieved typically in two ways. Manufacturing tolerances in the length of the cannula sheath and/or of the inner tubular lumen can result in such variation. This can be partially overcome by restricting the manufacturing dimensional variations that will be accepted. When the cannula sheath mates against the support body, any variation in the final position of the mated parts from a desired position can cause the above undesired distance variation. In the prior art apparatus the cannula sheath generally mates in a conical press-fit over an extension of the main support body. As in the case with most conical press-fit joints, there is often considerable variation in the final position. This is caused both by tolerance in the tapers of the sheath and body and also by variations in manual pressure employed to mate the sheath against the body. One prior art apparatus employs a resilient material for the support body and its extension. The resiliency of this structural element can also cause undesirable dimensional variations in the assembled apparatus.

The second disadvantage of the prior art apparatus is in the excessive volume of the introduction chamber for the anti-coagulant material. In a typical double lumen cannula apparatus the space in the funnel portion of the cannula sheath between the support body and the junction between the funnel and tubular portions of the cannula sheath forms an introduction chamber for such material. In normal use the cannula sheath is inserted first into a blood vessel. Blood begins to flow through the tubular portion and into the funnel section of the cannula sheath. The catheter portion consisting of a support body, a first conduit forming the inner tubular lumen and a second concuit to provide the anti-coagulant material is then inserted into the cannula sheath with the cannula sheath mating against the support body. The volume of blood initially in the cannula sheath and especially in the funnel portion occupies the space intended for introduction of the anti-coagulant material and should be minimized so that it will not begin to coagulate before being contacted by the anti-coagulant material. This volume has considerable variation in the prior art apparatus.

There is thus a need for double lumen cannula apparatus having improved control over the dilution of a blood sample with an anti-coagulant material and also having minimal volume for a chamber introducing the anti-coagulant to the cannula sheath.

SUMMARY OF THE INVENTION

In accordance with the present invention, double lumen cannula apparatus for blood sampling is provided comprising in combination a body member comprising a base and an extension projection from said base, said extension having a frustoconical shaped portion; a cannula sheath of generally funnel shape having a frustoconical portion of larger diameter than and coaxially surrounding that of said extension, said frustoconical portion of said sheath terminating at its reduced diameter end in a cylindrical tubular end portion; means affording an annular fluid-tight seal between said extension and said sheath; first conduit means traversing and having a fixed positional relationship with respect to said body member, said conduit means terminating in a tubular end portion spaced substantially coaxially within said reduced diameter tubular end portion of said sheath and having an end spaced a predetermined distance axially inwardly from the end of the surrounding reduced diameter sheath portion; cooperable abutment means on said body member and sheath defining said predetermined distance between said ends of said first conduit means and sheath; and second conduit means traversing said body member and opening into the space between said extension and the frustoconical portion of said sheath.

DESCRIPTION OF THE INVENTION

Figure 1:
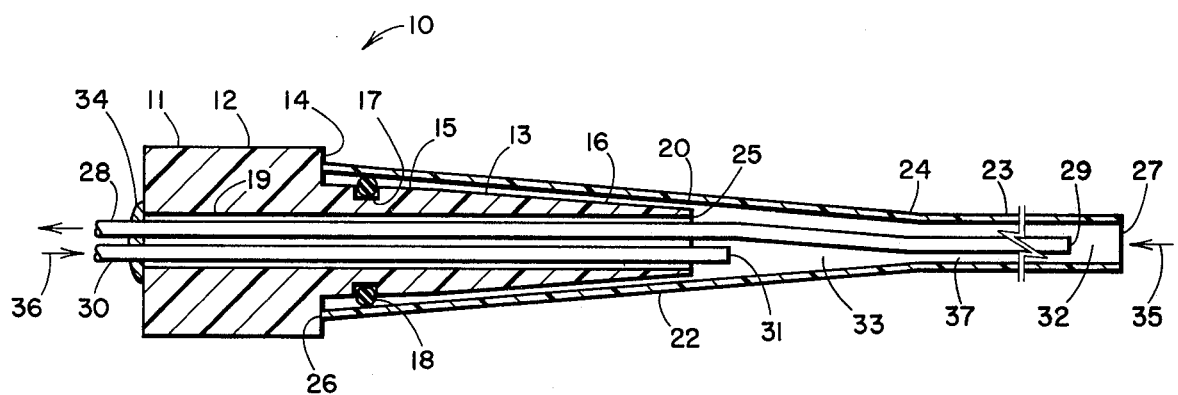
FIG. 1 is a vertical cross-sectional view of one illustrative embodiment of double lumen cannula apparatus of the present invention.

Referring to the Figure, the apparatus 10 has a body member 11 having a generally cylindrical base 12 and a tapered extension 13 projecting from said base 12. Extension 13 is of reduced cross-sectional area joining base 12 to form an abutment 14. Extension 13 is generally of frustoconical shape having an end 25. Extension 13 preferably has a frustoconical portion 15 joining base 12 and a frustoconical portion 16 of increased taper attached thereto. Extension 13 has a peripheral groove 17, preferably in the frustoconical portion 15, in which an annular gasket 18, such as an O-ring, is located. Body member 11 has an axial passage 19 extending longitudinally through base 12 and extension 13.

A hollow cannula sheath 20 having a generally funnel shape with a frustoconical portion 22 and a cylindrical tubular end portion 23 of reduced internal diameter joining the frustoconical portion 22 at junction 24 is mated against body member 11. The taper of extenson 13 and especially of frustoconical portion 15 is generally complementary to that of frustoconical portion 22 of sheath 20. The funnel or frustoconical portion 22 of cannula sheath 20 has an end 26 and the cylindrical tubular end portion 23 has a tip 27. End 26 contacts abutment 14. Gasket 18 contacts the inner surface of the wall of the funnel portion of cannula 20 along extension 13 to form a fluid-tight seal between extension 13 and cannula sheath 20. Since the cannula sheath 20 fits loosely over extension 13, except where contact is made with gasket 18, it is possible to reproducibly mate end 26 of cannula sheath 20 against abutment 14. Cannula sheath 20 can also be easily removed from body member 11 if desired.

A first conduit 28 extends through axial passage 19 and coaxially through the cylindrical tubular end portion 23 of cannula sheath 20 and has an end 29 located within tubular end portion 23 at a desired distance from tip 27 of tubular end portion 23. The volume inside cannula sheath 20 from end 29 to tip 27 is defined as the mixing chamber 32.

A second conduit 30 extends through axial passage 19 and terminates at end 31 slightly beyond end 25 of extension 13. The volume contained within cannula sheath 20 from end 25 of extension 13 to the junction 24 is defined as the introduction chamber 33.

The space around conduits 28 and 30 at the entrance to axial passage 19 is sealed in a fluid-tight relation with sealing material 34 which also maintains said conduits in a fixed positional relationship to body member 11.

The body member 11, cannula sheath 20 and conduits 28 and 30 are preferably fabricated from well-known organoplastics, such as polyethylene or polymerized caprolactam. It is further preferred that body member 11 be fabricated from a non-resilient or substantially rigid organoplastic, such as polyformaldehyde.

In the practice of the subject invention, the overall length of cannula sheath 20 is maintained as constant as possible during manufacture. With the cannula sheath 20 mated onto extension 13 with end 26 cooperably abuting against abutment 14, the length of conduit 28 is adjusted during manufacture so that end 29 is at a desired distance from tip 27. With a cannula tubular portion internal diameter of about 0.3 mm., this mixing distance is preferably about 2.5 mm. The length of extension 13 is selected during manufacture so as to minimize the distance from end 25 to junction 24 and thus minimize the volume of introduction chamber 33.

It is also understood that conduits 28 and 30 could pass through body member 11 in separate substantially parallel longitudinal axial passages instead of through a single passage 19. Conduit 30 could also communicate with chamber 33 through the side of extension 13.

In the use of the apparatus of the present invention the cannula sheath 20 is inserted into a blood vessel (not shown) and the blood sample 35 enters cannula sheath 20 through tip 27. The catheter assembly combination of body member 11, conduit 28 and conduit 30 is then inserted into cannula sheath 20 as shown in the Figure. Anti-coagulant material 36 enters through conduit 30, passes through introduction chamber 33 and then through the annular lumen 37 formed between cannula tubular end portion 23 and conduit 28. The anti-coagulant 36 mixes with blood 35 in the mixing chamber 32 and a controlled dilution of the blood is obtained. The diluted blood sample then passes through the lumen formed by conduit 28 for subsequent processing and/or analysis.

The apparatus of the present invention is an improvement over the known prior art in the following features. By having the above dimensional features controlled during manufacture and by having the cannula sheath mate reproducibly against the abutment 14 of the body member 11, the volume of the mixing chamber 32 can be reproducibly controlled so as to achieve desired mixing between a blood sample and the anti-coagulant material whenever the body member 11 and conduit 28 are inserted into cannula sheath 20. By locating the end 25 of extension 13 as close as possible to the junction 24 of the frustoconical and tubular end portions of the cannula sheath 20, the volume of the introduction chamber 33 is minimized. This reduces the amount of blood that might start to coagulate before mixing with the anti-coagulant material and also reduces the blood that must be displaced by the anti-coagulant material before it reaches mixing chamber 32. The O-ring seal along the extension 13 compensates for manufacturing tolerances in cannula sheath internal diameter and still achieves a fluid tight seal between the cannula sheath 20 and the body member 11. Prior art simple press-fit mating between the cannula sheath and body did not have this flexibility.

What is claimed is:

1. A double lumen cannula apparatus for blood sampling comprising in combination a body member comprising a base and an extension projecting from said base, said extension having a frustoconical shaped portion; a cannula sheath of generally funnel shape having frustoconical portion of larger diameter than and coaxially surrounding that of said extension, said frustoconical portion of said sheath terminating at its reduced diameter end in a cylindrical tubular end portion; means affording an annular fluid-tight seal between said extension and said sheath; first conduit means traversing and having a fixed positional relationship with respect to said body member, said conduit means terminating in a tubular end portion spaced substantially coaxially within said reduced diameter tubular end portion of said sheath and having an end spaced a predetermined distance axially inwardly from the end of the surrounding reduced diameter sheath portion; cooperable abutment means on said body member and sheath defining said predetermined distance between said ends of said first conduit means and sheath; and second conduit means traversing said body member and opening into the space between said extension and the frustoconical portion of said sheath.

2. An apparatus according to claim 1 wherein said extension and said sheath have corresponding coaxial frustoconical portions.

3. An apparatus according to claim 2 wherein said means affording an annular fluid-tight seal is an O-ring disposed in a peripheral groove in said extension and extending between said extension and sheath.

4. An apparatus according to claim 1 wherein said first conduit means comprises a tube extending through an axially extending bore in the extension and projecting therefrom into said sheath tubular end portion.

5. An apparatus according to claim 4 wherein said second conduit means comprises a second tube which extends through the same bore in said extension as said first mentioned tube.

6. An apparatus according to claim 1 wherein the second conduit means comprises a tube which extends through an axially extending bore in said extension.

7. Apparatus according to claim 1 wherein said sheath is removable from said body member.

* * * * *